United States Patent [19]

Bellhouse et al.

[11] Patent Number: 4,682,887
[45] Date of Patent: Jul. 28, 1987

[54] OPTICAL ASSAY FOR STORED HUMAN PLATELETS

[75] Inventors: Brian J. Bellhouse, The Lodge, North Street, Islip, Oxfordshire; John W. Stairmand, Wirral, both of England

[73] Assignee: Brian J. Bellhouse, Islip, England

[21] Appl. No.: 666,390

[22] Filed: Oct. 30, 1984

[30] Foreign Application Priority Data

Oct. 31, 1983 [GB] United Kingdom ............... 8328979

[51] Int. Cl.$^4$ .......................................... G01N 33/48
[52] U.S. Cl. ........................;............... 356/39; 356/427
[58] Field of Search .................................... 356/39–42, 356/338, 432–436, 440–442, 427; 250/573–576, 564–565

[56] References Cited

U.S. PATENT DOCUMENTS

| | | | |
|---|---|---|---|
| 3,733,136 | 6/1975 | Schuster et al. | 356/338 |
| 3,879,129 | 4/1975 | Inoue | 250/564 X |
| 3,891,325 | 5/1973 | Porath-Furedi | 356/39 X |
| 3,893,766 | 7/1975 | Hogg | 356/36 |
| 4,135,818 | 1/1979 | Kent et al. | 356/39 |
| 4,139,303 | 2/1979 | Carlson et al. | 356/39 |
| 4,201,470 | 5/1980 | Ehrly et al. | 356/39 |
| 4,227,814 | 10/1980 | Soodak et al. | 356/410 |
| 4,501,491 | 2/1985 | Breda et al. | 356/39 |
| 4,522,494 | 6/1985 | Bonner | 356/39 |

FOREIGN PATENT DOCUMENTS 0074428 3/1983 European Pat. Off. .
0095386 11/1983 European Pat. Off. .

OTHER PUBLICATIONS

Quantitative Measurements of Platelet Shape by Light Transmission Studies; Application to Storage of Platelets for Transfusion, Stein Holme and Scott Murphy, 1978.
"Blood Platelet Aggregometer: Predicted Effects of Aggregation Photometer Geometry, and Multiple Scattering", Applied Optics, vol. 22, No. 8, Apr. 15th, 1983.
"The Functioning of Blood Platelets", Scientific American, vol. 243, No. 8, Apr. 15th, 1983.
Abstract "A New Device for Evaluation of Platelets", presented Nov. 1981.

Primary Examiner—Vincent P. McGraw
Attorney, Agent, or Firm—Jeffers, Irish & Hoffman

[57] ABSTRACT

The viability of a pack of stored blood platelets is monitored by gripping the pack between two plates (6) and (7) which are closed to pinch together the walls of the bag (10) along an L-shaped seal (14), leaving a channel (17), squeezing a part (15) of the bag by means of a reciprocating plunger (19), so that the platelets continually flow to and fro between the part (15) and the part (16), through the channel (17), and passing a beam of light from an LED (27) through the channel (17), to a photoresistor (29). The AC signal from the photoresistor corresponds to the fluctuations in the intensity of the light passing through the channel (17) and the amplitude of this signal is representative of the viability, and hence the clinical acceptability, of the platelets.

4 Claims, 5 Drawing Figures

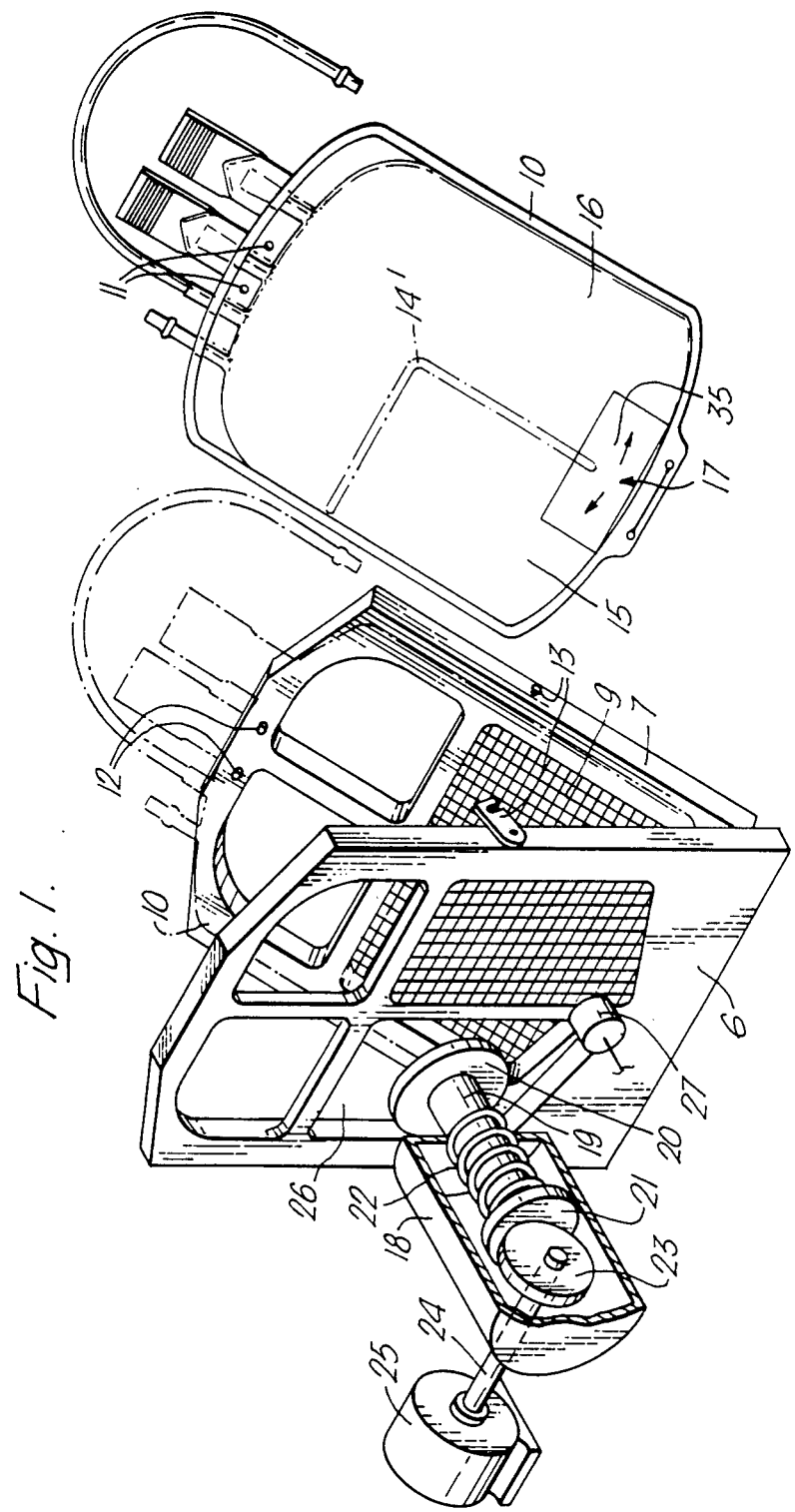

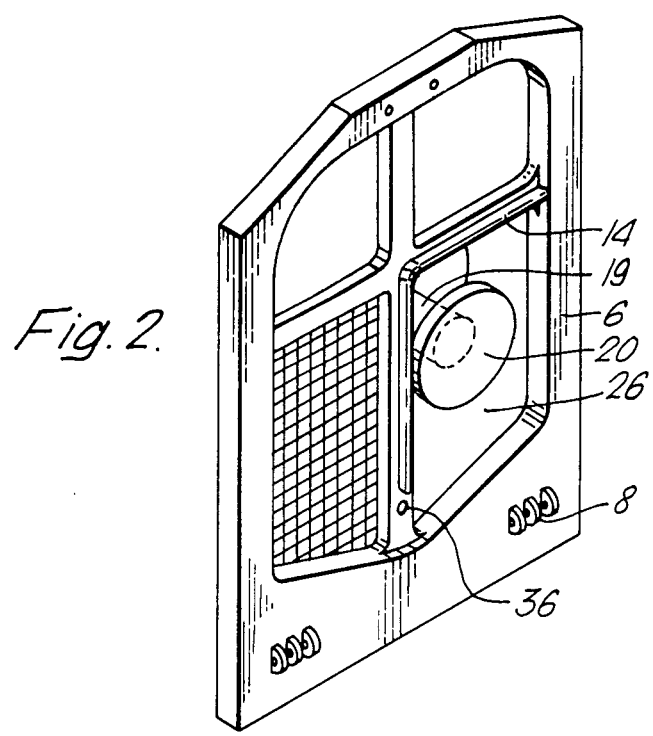
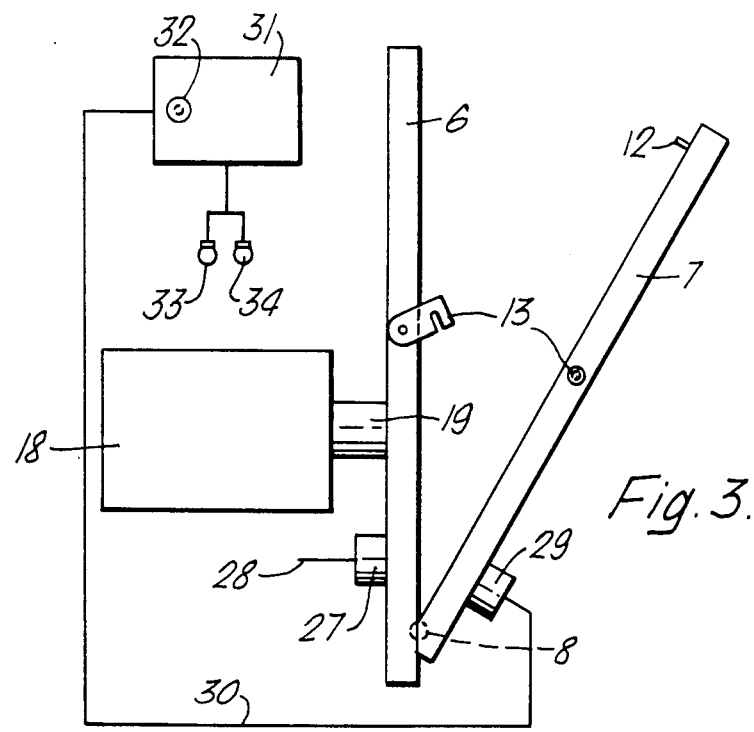

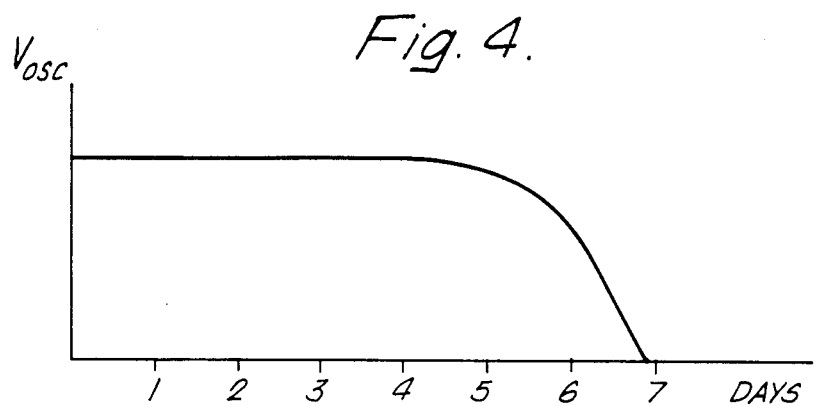
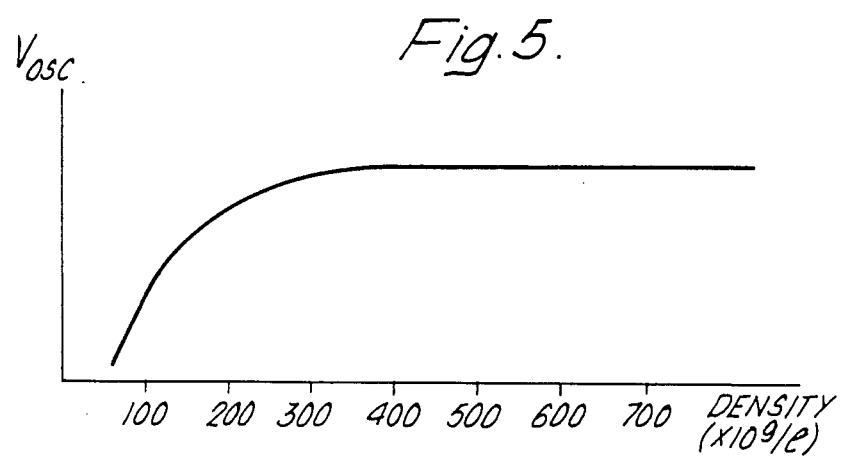

OPTICAL ASSAY FOR STORED HUMAN PLATELETS

BACKGROUND OF THE INVENTION

Concentrates of blood platelets in plasma are infused into patients to treat bleeding problems. Human platelets can withstand storage for only up to five days before progressive loss of platelet viability negates further clinical use. The lifetimes of stored platelets are highly variable, so it is inevitable that some useless platelets are given to patients while other packs of viable platelets are disposed of needlessly at the end of their arbitrary shelf life. Unfortunately, there is not in use any test of platelet viability which can be used without removing a sample of platelets from the pack. This is inconvenient, time consuming and involves the risk of the pack contents becoming infected.

Recently, an optical technique has been proposed for the measurement of platelet viability without withdrawing samples from the pack. The technique depends on the light scattering properties of the platelets which differ when the platelets are functional or dead. It is believed that this effect stems from the change of shape of platelets during storage. Functional platelets have a discoid shape. As the platelets age, more and more of them lose their discoid shape and become nearly spherical, thereby changing their light scattering property. The previously proposed technique has involved a comparison of the light scattering properties of the platelets when they are flowing and when they are stationary. Thus, when a beam of light is incident on a pack of the platelets, it has been found that the ratio of the intensity of light scattered in a particular direction when the platelets are moving, divided by the intensity of light scattered in the same direction when the platelets are still, may be less than 0.7 when the platelets are functional but approaches unity as the platelets die. This technique is of theoretical interest but its application would be difficult in clinical use as it would be necessary to remove a pack of platelets from the rocking tray, on which such packs are normally stored to keep the platelets in motion, and to transfer it to some device in which the light scattering properties could be measured both when the platelets are in motion and stationary.

SUMMARY OF THE INVENTION

A further characteristic of the optical properties of the platelets has now been appreciated by one of the present inventors. This is that the amplitude of fluctuations of the fluctuating light transmitted through the sack of moving platelets in a particular direction remains substantially constant for up to a day when the platelets are fresh, but then gradually decays nearly to zero as the platelets die. The mean amplitude of the transmitted light varies from sample to sample but in all cases the decay in the amplitude of the fluctuations follows a similar curve.

This novel appreciation leads to a method of monitoring non-invasively the viability of a pack of stored platelets, the method comprising agitating the pack, irradiating the pack with a beam of light, and detecting the amplitude of the fluctuations in the intensity of light transmitted through the pack of platelets in a particular direction and comparing this with a datum related to the amplitude of the fluctuations in the intensity of light transmitted in the same direction from a similar pack of fresh platelets under similar conditions.

A blood platelet monitoring assembly for carrying out the new method comprises at least one translucent pack of blood platelets; means for agitating the pack; a light source for irradiating the pack, while the pack is being agitated, with a beam of light; a photoelectric element for collecting light transmitted through the pack in a particular direction; and means responsive to an AC component, corresponding to fluctuations in the intensity of the transmitted light, in the output signal from the photoelectric element.

The particular advantage of the new method is that the viability of the new platelets can be monitored while the packs are being agitated, which is the accepted condition in order to prolong the life of the platelets.

Preferably, the pack is agitated to cause the platelets to flow continually to and fro across a zone through which the pack is irradiated with the light beam. The agitation could be provided by rocking the pack, for example in association with a tray similar to those on which platelet packs are conventionally stored. The frequency of the fluctuations in the amplitude of the transmitted light will be twice the frequency of the oscillating flow.

In the usual case in which the pack comprises a bag with two major, generally translucent, opposed walls, the bag may be supported so that these walls are pinched together to divide the interior of the bag into two parts connected by a channel constituting the zone; one of the parts being periodically squeezed to cause the to and fro flow through the channel. The channel is then preferably positioned adjacent to the bottom of the bag, as oriented in its support, so that any tendency of the platelets to sediment at the bottom of the bag is avoided by the continual disturbance of the platelets by the oscillating flow.

The earlier proposed optical technique used, as a light source, a bulky laser which was housed, together with plates between which the pack under test was sandwiched, in a light proof housing. The laser beam was directed through windows in the plates, and through the intervening pack, to the photoelectric element. This is all unacceptably cumbersome for clinical use. In order to carry out the new method, it is now proposed to utilise a device comprising two surfaces between which the pack of platelets under test is gripped, one of the surfaces incorporating a light source, such as light emitting diode, and the other incorporating, in a position opposite the light source, a photoelectric element, such as a photodiode or a photoresistor. This device is extremely compact, requires no screening from exterior light, and ensures that the optical system is correctly aligned as soon as the pack is gripped between its surfaces.

The datum reading might be read by a technician and recorded when the pack is fresh, preferably within twelve hours of the platelets having been obtained from a human body. Prior to clinical use, a second reading would be taken by the technician, and the platelets may then be considered to be sufficiently non-functional for clinical use, if the amplitude of the fluctuations has decreased to say 25% or less of the datum figure for fresh platelets. An appropriate display would then merely need to provide a numerical reading representing the amplitude of the AC signal. Alternatively, appropriate circuitry may incorporate a microprocessor or other intelligent circuit which stores the datum signal corresponding to the pack when fresh, and provides a continuous display representing the ratio of the current signal to the datum signal. In the simplest case, this may be a green light which is illuminated when the platelets are still functional and a red light when they are not.

Surprisingly, a datum reading for each pack when fresh may be unnecessary. This is because, first, until the number of live platelets has dropped to a very low level, the amplitude of the fluctuations in the transmitted light is almost independent of the density or volume of live platelets in the pack, and, secondly, because the reduction in the amplitude of the fluctuations diminishes very quickly when an appreciable proportion of the platelets become non-viable. It follows that, for a particular optical system, infrequent calibration is all that is necessary to provide a preset threshold corresponding to the amplitude of the fluctuations in the intensity of the transmitted light, below which there are insufficient living platelets for the pack to be clinically functional. The light or other display can then be arranged merely to indicate whether the amplitude of the AC signal is above or below the preset threshold.

BRIEF DESCRIPTION OF THE DRAWINGS

An example of an optical assay system in accordance with the invention is illustrated diagrammatically in the accompanying drawings, in which:

FIG. 1 is an exploded, partially cut away, perspective view;

FIG. 2 is a perspective view of a plate of a pack supporting device;

FIG. 3 is an elevation of the system; and,

FIGS. 4 and 5 are relevant graphs.

DETAILED DESCRIPTION OF A PREFERRED EMBODIMENT

As shown in FIG. 1, the system incorporates a device comprising a first, vertical fixed plate 6, and a similar plate 7 which is connected to it by a hinge 8. Each plate consists of a peripheral frame formed integrally with a central cruciform portion defining with the peripheral frame, four windows. In each case the upper windows are open. The lower windows of the plate 7 and one of the windows of the plate 6 are partially closed by screens 9. The plate 7 is arranged to be swung up generally parallel to the plate 6, about the hinge 8, to grip between the two plates a conventional bag 10 of blood platelets in plasma, The bag has, in a peripheral seam, holes 11 which are fitted onto pegs 12 projecting from the plate 7. The two plates 6 and 7 are held closed, with the bag 10 gripped between them, by means of side catches 13. FIG. 1 shows the bag in full lines separate from the plates and, in chain dotted lines, in position on the plate 7.

With the bag positioned between the plates an L-shaped seal 14 pinches the bag along a pinch line shown at 14' in dotted lines in FIG. 1, to divide the interior of the bag into parts 15 and 16, which are interconnected by a channel 17 adjacent to the bottom of the bag.

Mounted on a common base with the plate 6 is a cylindrical housing 18 in which there slides axially a plunger 19 carrying at one end a disc 20 and at the other end a disc 21. A helically coiled compression spring 22 acts between the disc 21 and an end wall of the housing 18 to urge the disc 20 to a withdrawn position away from the plate 6. A cam 23, which is fixed on a shaft 24, driven at constant rotational speed by an electric motor 25, periodically moves the plunger 19 and hence the disc 20 through an open lower window 26 in the plate 6, against the action of the spring 22, to squeeze the part 15 of the bag 10. This displaces the contents of the bag, through the channel 17 up into the part 16. As the cam 23 rotates to its smaller radius orientation relative to the disc 21, the plunger 19 and disc 20 are able to move back out of the plate 6 under the action of the spring 22, thus releasing the squeeze pressure on the part 15 of the bag 10. The differential hydrostatic pressure at the channel 17, resulting from the previous displacement of the contents into the part 16 of the bag 10, then causes the contents to flow back through the channel 17 into the part 15. This periodic rotation of the cam 23 thus causes to and fro flow in the bag 10 through the channel 17, as indicated by the arrows, and keeps all the contents in continual motion. The frequency of the cam 23 may be about 2 Hz and the stroke of the disc 20 about 3 ml.

In alignment with the channel 17, the plate 6 carries a cylindrical mounting 27, incorporating a light emitting diode (Hewlett-Packard HLMP 3750, wavelength 635 nm), which is energised through a line 28. The LED directs its beam through an opening 36 in the plate 6, and through the channel 17 in the bag 10, where it is scattered by the platelets. Any light which is ultimately transmitted in the straight ahead direction, passes through a complimentary opening in the plate 7, and is picked up by a light sensitive resistor in a cylindrical mounting 29. The electrical output of the photoresistor, which will correspond directly to the amplitude of the light transmitted at an angle of substantially 0° to the beam from the LED, is transmitted along a line 30 to a microprocessor 31. This microprocessor deduces the AC component in the signal by sensing and subtracting the maximum and minimum signal levels.

As platelets in the bag 10 are caused to flow with an oscillating motion to and fro through the channel 17, the platelets will, at maximum velocity, be caused to stream in mutual alignment through the channel, and, upon reversal of the direction of flow, will adopt a relatively random orientation. This is what leads to the fluctuations of the amplitude in the intensity of light received from the LED by the photoresistor.

A display of the microprocessor 31 may be preset to respond to an AC signal having an amplitude above or below a certain threshold corresponding to an acceptable or unacceptable number of viable platelets in the bag 10, respectively. Alternatively, if a pack is tested when the platelets are fresh, the microprocessor 31 may be instantly calibrated to a corresponding threshold, by recording the datum reading by, for example, depression of a switch 32. In either case, when the amplitude is above the threshold, indicating that the platelets are viable, a green lamp 33 may be illuminated. When the bag of platelets has become effectively non-functional, the amplitude will fall below the threshold, and a red lamp 34 will be illuminated. In this way any particular bag of platelets can be used up to a last possible moment when a satisfactory proportion of its platelets are viable for clinical use.

FIG. 4 shows a graph of the variation in a voltage $V_{osc}$ corresponding to the amplitude of the AC component in the signal from the photoresistor, with a period of days. The sharp cut off after, on average, five days, is very noticeable.

FIG. 5 shows a variation in a similar voltage with a variation in the density of viable platelets in the bag 10. This shows that the amplitude of the AC signal is substantially independent of the density when the density is between 300 and 700 times $10^9/1$, and falls off very sharply at lower densities. Although variations in the density and indeed in the volume of platelets in a typical bag 10 occur, dependent upon the fraction of the centrifuged blood which is encapsulated in that bag, any bag of viable platelets can be expected to have a density within this range 300 to 700.

The walls of the bag 10 are conventionally of calendered plastics which is translucent but the wall surfaces are rough and may produce unwanted scattering of the light beam, even to the point of obscuring the scattering by the platelets. The plasma wets the inner surfaces of the bag walls but the problem remains at the outer wall surfaces. To overcome this and provide an optically clear window through each bag wall, a patch of optically clear tape 35 with a coating of an optically clear adhesive is stuck on the outer surface of each bag wall in alignment with the channel 17.

A bank of illustrated devices may be set up alongside one another and driven via a common camshaft 24, and may be coupled to a common signal processor and display.

What is claimed is:

1. A device for use in a blood platelet monitoring assembly of the kind comprising at least one translucent pack of blood platelets comprising:

means for periodically agitating the pack to cause platelets in the pack to flow, said means for agitating including first and second surfaces between which the pack of platelets is adapted to be gripped, light source means in one of said surfaces for irradiating the pack with light and causing light to be transmitted through the pack in a given direction, photoelectric means in the other of said surfaces in a position opposite to said light source means for collecting the light transmitted in said given direction and producing an electrical signal having an AC component with an amplitude equal to the difference between minimum and maximum levels of transmitted light, said AC component having a frequency equal to the frequency of periodic agitation, and means responsive to said signal for extracting the AC component thereof, comparing the amplitude of the AC component with a reference datum and generating a visual display indicating one of acceptability or non-acceptability of the viability of the pack.

2. A device according to claim 1, wherein said surfaces are the inner faces of two hinged plates.

3. A device according to claim 1, wherein said surfaces are shaped to pinch together opposed walls of said pack to divide the interior of said pack into two parts connected by a channel situated between said light source and said photoelectric element; and means are provided for periodically squeezing only one of said parts and alternately releasing said one of said parts without pressing the other of said parts to cause said platelets in said pack to flow to and fro through said channel.

4. A device according to claim 1, wherein said light source is a light emitting diode and said photoelectric element is a photoresistor.

* * * * *